United States Patent
Bachmann et al.

(10) Patent No.: US 7,105,692 B2
(45) Date of Patent: Sep. 12, 2006

(54) CRYSTALLINE MODIFICATION OF A MANGANESE COMPLEX

(75) Inventors: Frank Bachmann, Freiburg (DE); Hanspeter Baier, Grenzach-Wyhlen (DE); Christof Dosenbach, Bad Bellingen (DE); Marie-Josée Dubs, Wittersdorf (FR); Tassilo Habereder, Krailling (DE); Menno Hazenkamp, Riehen (CH); Uwe Heinz, Saarlouis (DE); Cornelia Makowka, Laufenburg (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/542,722

(22) PCT Filed: Jan. 19, 2004

(86) PCT No.: PCT/EP2004/000359

§ 371 (c)(1),
(2), (4) Date: Jul. 20, 2005

(87) PCT Pub. No.: WO2004/065302

PCT Pub. Date: Aug. 5, 2004

(65) Prior Publication Data

US 2006/0079705 A1    Apr. 13, 2006

(30) Foreign Application Priority Data

Jan. 24, 2003    (EP)    ................... 03405032

(51) Int. Cl.
*C07F 13/00*    (2006.01)
*C11D 1/83*    (2006.01)
*C11D 3/26*    (2006.01)
*C11D 3/39*    (2006.01)
*C11D 3/395*    (2006.01)

(52) U.S. Cl. ............... 556/32; 510/311; 510/372; 510/376; 252/186.33

(58) Field of Classification Search ................ 556/32; 510/311, 372, 376; 252/186.33
See application file for complete search history.

(56) References Cited

U.S. PATENT DOCUMENTS

| | | | |
|---|---|---|---|
| 6,242,405 B1 | 6/2001 | Lykke et al. ............... 510/321 |
| 6,800,775 B1 * | 10/2004 | Bachmann et al. .......... 556/34 |
| 6,825,162 B1 * | 11/2004 | Hazenkamp et al. ........ 510/457 |
| 6,828,293 B1 | 12/2004 | Hazenkamp et al. ........ 510/376 |
| 6,982,243 B1 * | 1/2006 | Hazenkamp et al. ........ 510/311 |
| 2003/0100763 A1 * | 5/2003 | Beck et al. ................... 546/2 |
| 2004/0142843 A1 | 7/2004 | Schlingloff et al. ......... 510/312 |

FOREIGN PATENT DOCUMENTS

| | | |
|---|---|---|
| DE | 44 43 177 | 6/1996 |
| EP | 0 902 083 | 3/1999 |
| EP | 0 955 289 | 11/1999 |
| WO | 00/03574 | 1/2000 |
| WO | 02/02865 | 1/2002 |
| WO | WO 2004/065302 A2 * | 8/2004 |
| WO | WO 2004/099357 A1 * | 11/2004 |

(Continued)

OTHER PUBLICATIONS

Chandra et al., J. Chem. Soc. Dalton Transactions, Issue 6, 1993, pp. 863-869.*

(Continued)

*Primary Examiner*—Porfirio Nazario-Gonzalez
(74) *Attorney, Agent, or Firm*—Mervin G. Wood

(57) ABSTRACT

This invention relates to a novel crystal form of the 1:1 manganese (III) complex of N,N',N"tris[salicylideneaminoethyl]amine, a process for its preparation and the use thereof.

14 Claims, 2 Drawing Sheets powder X-ray diffraction pattern of Mn(III)saltren (compound (2)), obtained from Example 1.

FOREIGN PATENT DOCUMENTS

WO    WO 2004/104155 A1 * 12/2004

OTHER PUBLICATIONS

Drew et al., J. Chem. Soc., Chem. Commun., 1995, pp. 1035-1038.*
Cook et al., J. Chem. Soc. Dalton Transactions, Issue 14, 1976, pp. 1369-1375.*
English Lang. Abst. from esp@cenet web site printed Jan. 2006 of WO 00/03574.
English Lang. Abst. from esp@cenet web site printed Jan. 2006 of EP 0 955 289.
English Lang. Abst. from esp@cenet web site printed Jan. 2006 of DE 44 43 177.
Cook et al., J. Chem. Soc. Dalton Trans, 1976 pp. 1369-1375.
Ramesh et al., J. Chem. Soc. Dalton Trans, 1991 pp. 2917-2920.
Chandra et al., J. Chem. Soc. Dalton Trans. 1993, pp. 863-869.
Inorg. Chem. vol. 30, 1991, pp. 3795-3798.

* cited by examiner

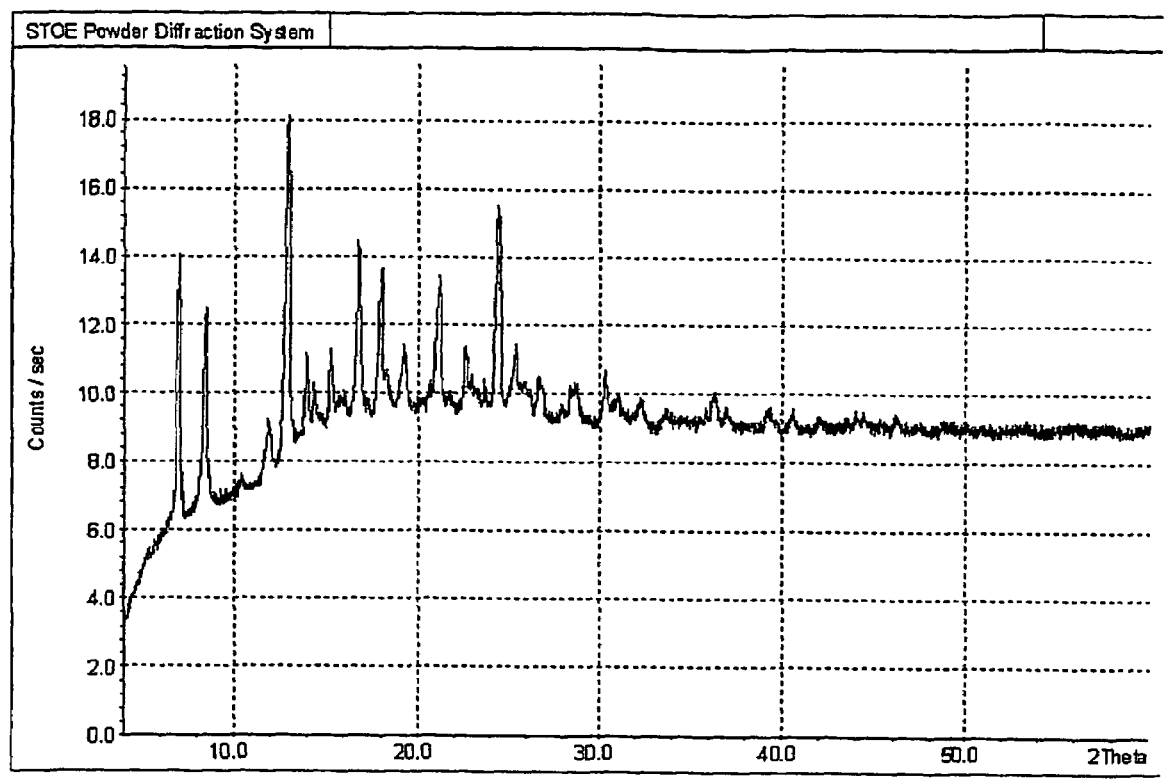
Fig.1: powder X-ray diffraction pattern of Mn(III)saltren (compound (2)), obtained from Example 1.

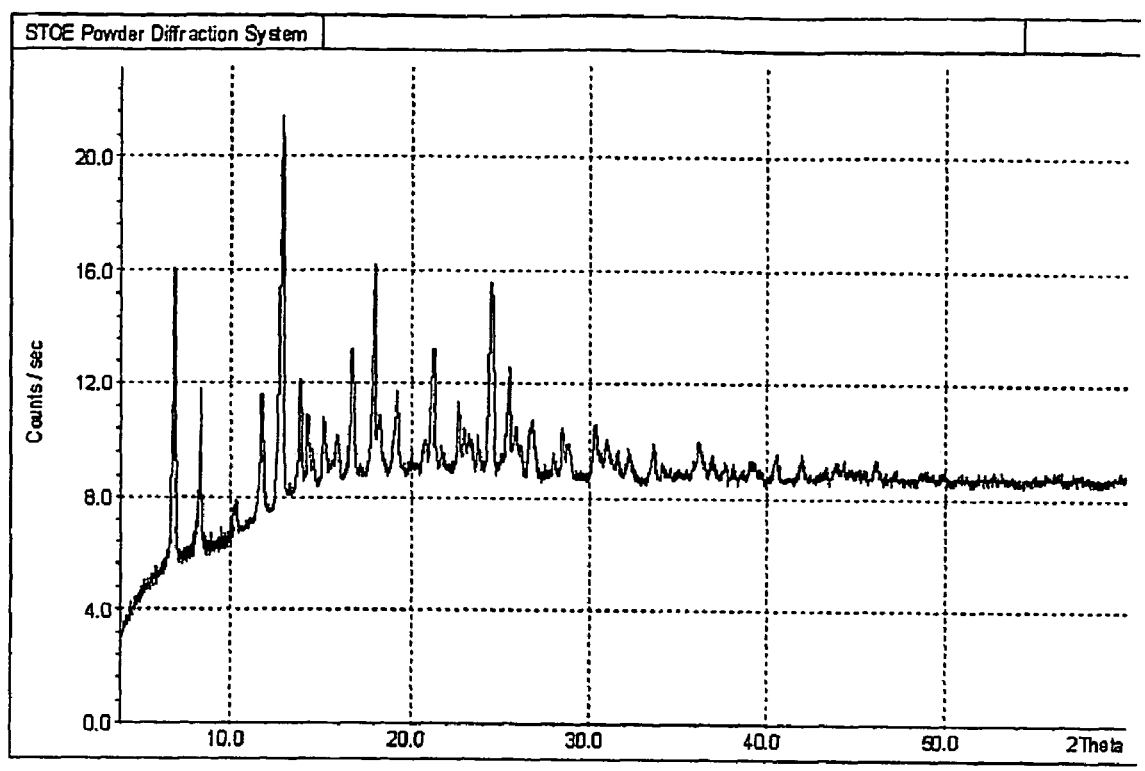
Fig. 2.: powder X-ray diffraction pattern of Mn(III)saltren (compound (2)), obtained from Example 2

CRYSTALLINE MODIFICATION OF A MANGANESE COMPLEX

This application is the National Stage of International Application PCT/EP04/000359, filed on Jan. 19, 2004.

This invention relates to a novel polymorph crystal form of the 1:1 manganese (III) complex of N,N',N''-tris[salicylideneaminoethyl]amine, a process for its preparation and the use thereof.

N,N',N''-tris[salicylideneaminoethyl]amine (saltren)

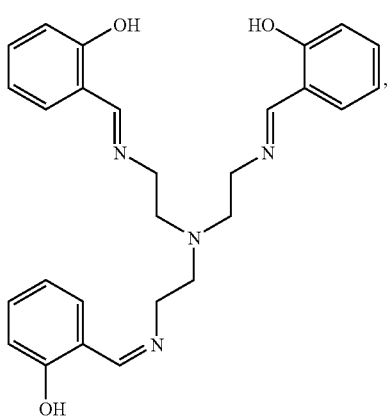

(1)

the 1:1 manganese(III) complex (Mn(III)saltren) thereof

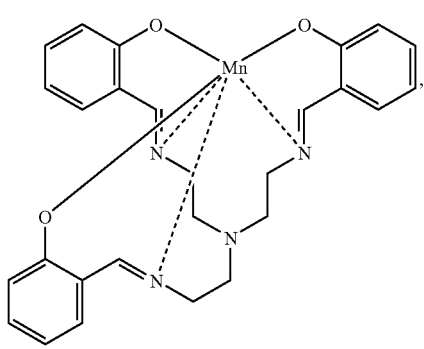

(2)

its production as well as its use as peroxygen catalyst are known for example from WO0105925 (Examples 1 and 13), WO0109276 (Example 53) and WO02059245 (Example 15). The Mn(III) saltren compound has been known and producible as an amorph modification only.

The ability of a substance to exist in more than one crystal form is defined as polymorphism and these different crystal forms are named "polymorph modifications" or "polymorphs". In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs.

The different polymorphs of a substance possess different energies of the crystal lattice and, thus, in solid state they show different physical properties such as form, density, melting point, colour, stability, dissolution rate, milling facility, granulation, compacting etc.

Surprisingly a new crystal modification of the 1:1 manganese (III) complex of N,N',N''-tris[salicylideneaminoethyl]amine

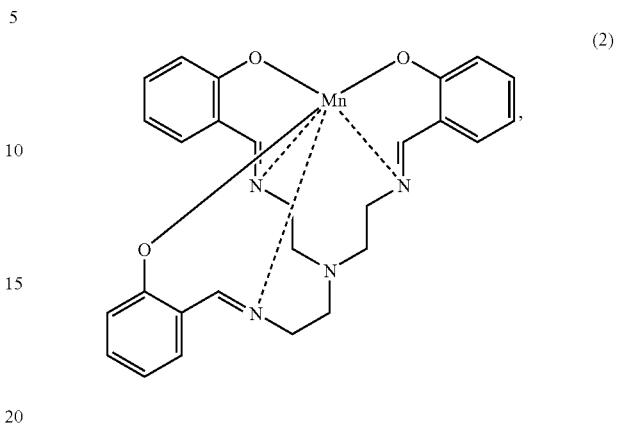

(2)

which is characterized by a peak at a d-spacing of about 6.87 Å in its powder X-ray diffraction pattern, has been found.

Specifically, the new crystal modification of the 1:1 manganese (III) complex of N,N',N''-tris[salicylideneaminoethyl]amine (compound (2)) is characterized by peaks with d-spacings of about 6.87 and 12.69 Å in its powder X-ray diffraction pattern.

More specifically, the new crystal modification of the 1:1 manganese (III) complex of N,N',N''-tris[salicylideneaminoethyl]amine (compound (2)) is characterized by peaks with d-spacings of about 3.51, 3.65, 4.20, 4.63, 4.95, 5.30, 6.38, 6.87, 7.50, 10.57 and 12.69 Å in its powder X-ray diffraction pattern.

Very specifically, the new crystal modification of the 1:1 manganese (III) complex of N,N',N''-tris[salicylideneaminoethyl]amine (compound (2)) is characterized by peaks with d-spacings of about 2.22, 2.48, 2.94, 3.14, 3.51, 3.65, 3.76, 3.94, 4.20, 4.63, 4.95, 5.30, 5.82, 6.19, 6.38, 6.87, 7.50, 8.59, 10.57 and 12.69 Å in its powder X-ray diffraction pattern.

The powder sample of the new crystal modification of Mn(III)saltren (compound (2)) has been analysed by a STOE-powder-diffractometer at room temperature (25° C.) under Cu X-ray [$\lambda(CuK\alpha)$=1.540598 Å].

Table 1 shows the characteristic spacing between the lattice planes designated by d and expressed in Angstrom units [Å] and their corresponding characteristic relative intensity (weak, medium or strong).

TABLE 1

| d(Å) | Intensity |
| --- | --- |
| 12.69 | strong |
| 10.57 | medium |
| 8.59 | weak |
| 7.50 | medium |
| 6.87 | strong |
| 6.38 | medium |
| 6.19 | weak |
| 5.82 | weak |
| 5.30 | medium |
| 4.95 | medium |
| 4.63 | medium |
| 4.20 | medium |
| 3.94 | weak |
| 3.76 | weak |
| 3.65 | medium |
| 3.51 | medium |

TABLE 1-continued

| d(Å) | Intensity |
|---|---|
| 3.14 | weak |
| 2.94 | weak |
| 2.48 | weak |
| 2.22 | weak |

FIG. 1. shows the powder X-ray diffraction pattern of Mn(III)saltren (compound (2)), obtained from Example 1. The values are given in 2θ.

FIG. 2. shows the powder X-ray diffraction pattern of Mn(III)saltren (compound (2)), obtained from Example 2. The values are given in 2θ.

The following formula shows the relation between d and 2θ:

$$d(\text{Å}) = \frac{1.54060 \text{ Å}}{2\sin(2\theta/2)}$$

In addition, by recording a single crystal of the new crystal modification of Mn(III)saltren (compound (2)) in a STOE Stadi 4-circle-diffractometer D045 under Mo X-rays [λ(MoK$_\alpha$)=0.71073 Å] at 293 K, there were obtained the basic crystallographic data for a single cell.

The size of the crystal has been 0.5 mm×0.35 mm×0.2 mm.

The basic crystallographic data (diffraction on single crystal) for the new crystal modification of Mn(III)saltren (compound (2)) are shown in Table 2.

TABLE 2

| Crystal system | Monoclinic |
|---|---|
| Space group | P 2$_1$/n |
| a[Å] | 7.906 |
| b[Å] | 25.609 |
| c[Å] | 11.736 |
| α[°] | 90 |
| β[°] | 96.55 |
| γ[°] | 90 |
| V[Å$^3$] | 2360.6 |
| Structure unit per cell (Z) | 4 |
| Absorption coefficient μ [mm$^{-1}$] | 0.597 |
| F(000) | 1064 |

In comparison to the amorph modification, the new crystal modification of Mn(III)saltren (compound (2)) has improved properties.

The new crystal modification posses for example improved formulation properties in comparison to the amorph modification. Further, the new crystal modification has an improved filterability.

The new crystal modification of Mn(III)saltren (compound (2)) can be used for improving the action of peroxides, for example in the treatment of textile material, without at the same time causing any appreciable damage to fibres and dyeings.

Peroxide-containing bleaching agents have been used in washing and cleaning processes for some time. They have an excellent action at a liquor temperature of 90° C. and above, but their performance noticeably decreases with lower temperatures. It is known that various transition metal ions, added in the form of suitable salts, or coordination compounds containing such cations catalyse the decomposition of H$_2$O$_2$. In that way it is possible to increase the bleaching action of H$_2$O$_2$, or of precursors that release H$_2$O$_2$, or of other peroxo compounds, the bleaching action of which is unsatisfactory at lower temperatures. Particularly significant for practical purposes are those combinations of transition metal ions and ligands the peroxide activation of which is manifested in an increased tendency towards oxidation in respect of substrates and not only in a catalase-like disproportionation. The latter activation, which tends rather to be undesirable in the present case, could impair the bleaching effects of H$_2$O$_2$ and its derivatives which are insufficient at low temperatures.

In respect of H$_2$O$_2$ activation having effective bleaching action, mononuclear and polynuclear variants of manganese complexes with various ligands, especially with 1,4,7-trimethyl-1,4,7-triazacyclononane and optionally oxygen-containing bridge ligands, are currently regarded as being especially effective. Such catalysts have adequate stability under practical conditions and, with Mn$^{n+}$, contain an ecologically acceptable metal cation, but their use is unfortunately associated with considerable damage to dyes and fibres.

The invention accordingly relates to the use of the new polymorph crystal modification of the 1:1 manganese (III) complex of N,N',N"-tris[salicylideneaminoethyl]amine (compound (2))

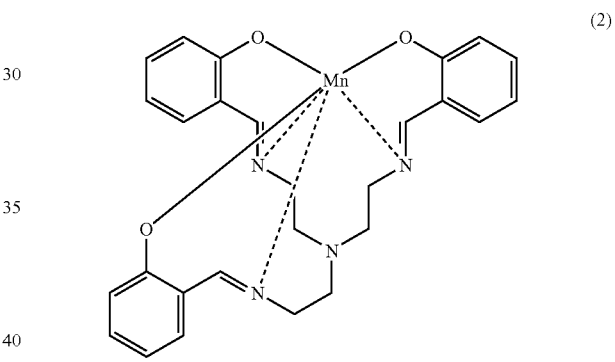

(2)

as catalyst for oxidation reactions.

The new crystal modification of the 1:1 manganese (III) complex of N,N',N"-tris[salicylideneaminoethyl]amine (compound (2)) is preferably used together with peroxy compounds. Examples that may be mentioned in that regard include the following uses:

a) the bleaching of spots or stains on textile material in the context of a washing process or a (pre-)soaking process;

b) the prevention of redeposition of migrating dyes during the washing of textile material;

c) the cleaning of hard surfaces, especially wall tiles or floor tiles, more especially for removing mold stains;

d) use in washing and cleaning solutions having an antibacterial action;

e) as pretreatment agents for bleaching textiles;

f) as catalysts in selective oxidation reactions in the context of organic synthesis;

g) as catalyst for the waste water treatment.

A further use relates to the use of the new crystal modification of the 1:1 manganese (III) complex of N,N', N"-tris[salicylideneaminoethyl]amine (compound (2)) as catalyst for reactions with peroxy compounds for bleaching in the context of paper-making. This relates especially to the bleaching of pulp, which can be carried out in accordance with customary processes. Also of interest is the use of the new crystal modification of the 1:1 manganese (III) complex of N,N',N"-tris[salicylidene-aminoethyl]amine (compound (2)) as catalyst for reactions with peroxy compounds for the bleaching of waste printed paper.

Preference is given to the bleaching of spots or stains on textile material, the prevention of the redeposition of migrating dyes in the context of a washing process, or the cleaning of hard surfaces, especially wall or floor tiles.

It should be emphasised that the new crystal modification of the 1:1 manganese (III) complex of N,N',N"-tris[salicylideneaminoethyl]amine (compound (2)) does not cause any appreciable damage to fibres and dyeings, for example in the bleaching of textile material.

Processes for preventing the redeposition of migrating dyes in a washing liquor are usually carried out by adding to the washing liquor, which contains a peroxide-containing washing agent, the new crystal modification of the 1:1 manganese (III) complex of N,N',N"-tris[salicylideneaminoethyl]amine (compound (2)) in an amount of from 0.1 to 200 mg, preferably from 0.2 to 75 mg, especially from 0.2 to 30 mg, per liter of washing liquor. The new crystal modification of the 1:1 manganese (III) complex of N,N',N"-tris[salicylideneaminoethyl]amine (compound (2)) can be used together with other transition metal complexes. Such complexes are described for example in WO02088289, WO0105925, WO0109276, WO02059245, WO053574, EP902083 and EP955289.

The present invention relates also to a washing or cleaning agent, comprising

I) 0–50 wt-%, preferably 0–30 wt-%, A) of at least one anionic surfactant and/or B) of at least one non-ionic surfactant,
II) 0–70 wt-%, preferably 0–50 wt-%, C) of at least one builder substance,
III) 0–10 wt-%, preferably 0–5 wt-% D) of at least one (poly)phosphonate and/or aminoalkylene-poly(alkylenephosphonate),
IV) 1–99 wt-%, preferably 1–70 wt-%, E) of at least one peroxide and/or of at least one peroxide-forming substance, and
V) F) the new crystal modification of the 1:1 manganese (III) complex of N,N',N"-tris[salicylideneaminoethyl]amine (compound (2)) in an amount which, in the liquor, gives a concentration of 0.2–50 mg/liter of liquor, preferably 0.2–30 mg/liter of liquor, when from 0.2 to 20 g/liter of the washing, cleaning, disinfecting and bleaching agent are added to the liquor.

Preferably, the present invention relates also to a disinfecting or bleaching agent, comprising I) 0–20 wt-%, preferably 0–15 wt-%, A) of at least one anionic surfactant and/or B) of at least one non-ionic surfactant,
II) 0–60 wt-%, preferably 0–50 wt-%, C) of at least one builder substance,
III) 0–10 wt-%, preferably 0–5 wt-% D) of at least one (poly)phosphonate and/or aminoalkylene-poly(alkylenephosphonate),
IV) 1–99 wt-%, preferably 1–70 wt-%, E) of at least one peroxide and/or of at least one peroxide-forming substance, and
V) F) the new crystal modification of the 1:1 manganese (III) complex of N,N',N"-tris[salicylideneaminoethyl]amine (compound (2)) in an amount which, in the liquor, gives a concentration of 0.2–50 mg/liter of liquor, preferably 0.2–30 mg/liter of liquor, when from 0.2 to 20 g/liter of the washing, cleaning, disinfecting and bleaching agent are added to the liquor.

The above percentages are in each case percentages by weight, based on the total weight of the agent. The agents preferably contain from 0.005 to 2 wt-% of the new crystal modification of the 1:1 manganese (III) complex of N,N',N"-tris[salicylideneaminoethyl]amine (compound 2)), especially from 0.01 to 1 wt-% and preferably from 0.02 to 1 wt-%.

When the washing or cleaning agents according to the invention comprise at least one component A) and/or B), the amount thereof is preferably 1–50 wt-%, especially 1–30 wt-%.

When the agents according to the invention comprise at least one component C), the amount thereof is preferably 1–70 wt-%, especially 1–50 wt-%. Special preference is given to an amount of from 5 to 50 wt-% and especially an amount of from 10 to 50 wt-%.

When the agents according to the invention comprise at least one (poly)phosphonate and/or aminoalkylene-poly(alkylenephosphonate), the amount thereof is preferably 0.1–3 wt-%, especially 1–3 wt-%. The preferred compounds are amino-trimethylene-phosphonic acid, diethylenetriamine penta(methylenephosphonic acid), ethylene diamine tetra(methylene phosphonic acid), as well as mixtures thereof and the salts therefrom.

Corresponding washing, cleaning, disinfecting or bleaching processes are usually carried out by using an aqueous liquor comprising a peroxide and from 0.1 to 200 mg of the new crystal modification of the 1:1 manganese (III) complex of N,N',N"-tris[salicylideneaminoethyl]amine (compound (2)) per liter of liquor. The liquor preferably contains from 0.2 to 30 mg of the compound of formula (2) per liter of liquor.

The agents according to the invention can be, for example, a peroxide-containing complete washing agent or a separate bleaching additive. A bleaching additive is used for removing coloured stains on textiles in a separate liquor before the clothes are washed with a bleach-free washing agent. A bleaching additive can also be used in a liquor together with a bleach-free washing agent.

It is also possible to prepare granules of the agent according to the invention, for example, by first preparing an initial powder by spray-drying an aqueous suspension containing all the components listed above except for components E) and F), and then adding the dry components E) and F) and mixing everything together. It is also possible to add component F) to an aqueous suspension containing components A), B), C) and D), then to carry out spray-drying and then to mix component E) with the dry mass.

It is also possible to start with an aqueous suspension that contains components A), C) and D), but none or only some of component B). The suspension is spray-dried, then component F) is mixed with component B) and added, and then component E) is mixed in in the dry state.

It is also possible to mix all the components together in the dry state.

The anionic surfactant A) can be, for example, a sulfate, sulfonate or carboxylate surfactant or a mixture thereof. Preferred sulfates are those having from 12 to 22 carbon atoms in the alkyl radical, optionally in combination with alkyl ethoxysulfates in which the alkyl radical has from 10 to 20 carbon atoms.

Preferred sulfonates are e.g. alkylbenzenesulfonates having from 9 to 15 carbon atoms in the alkyl radical. The cation in the case of anionic surfactants is preferably an alkali metal cation, especially sodium.

The anionic surfactant component may be, e.g., an alkylbenzenesulfonate, an alkylsulfate, an alkylethersulfate, an olefinsulfonate, an alkanesulfonate, a fatty acid salt, an alkyl or alkenyl ether carboxylate or an α-sulfofatty acid salt or an ester thereof. Preferred are alkylbenzenesulfonates having 10 to 20 carbon atoms in the alkyl group, alkylsulfates having 8 to 18 carbon atoms, alkylethersulfates having 8 to 18 carbon atoms, and fatty acid salts being derived from palm oil or tallow and having 8 to 18 carbon atoms. The average molar number of ethylene oxide added in the alkylethersulfate is preferably 1 to 20, preferably 1 to 10. The salts are preferably derived from an alkaline metal like sodium and potassium, especially sodium. Highly preferred carboxylates are alkali metal sarcosinates of formula R—CO ($R_1$)$CH_2COOM_1$ in which R is alkyl or alkenyl having 9–17 carbon atoms in the alkyl or alkenyl radical, $R_1$ is $C_1$–$C_4$ alkyl and $M_1$ is an alkali metal, especially sodium.

The nonionic surfactant component may be, e.g., primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

The total amount of anionic surfactant and nonionic surfactant in the washing or cleaning agent is preferably 5–50 wt-%, preferably 5–40 wt-% and more preferably 5–30 wt-%. As to these surfactants it is preferred that the lower limit is 10 wt-%.

The total amount of anionic surfactant and nonionic surfactant in the disinfecting or bleaching agent is preferably 0–15 wt-%.

Preferred carboxylates are alkali metal sarcosinates of formula $R_2$—CO—N($R_3$)—$CH_2COOM^{r1}$ wherein $R_2$ is alkyl or alkenyl having from 8 to 18 carbon atoms in the alkyl or alkenyl radical, $R_3$ is $C_1$–$C_4$alkyl and $M^{r1}$ is an alkali metal.

The non-ionic surfactant B) can be, for example, a condensation product of from 3 to 8 mol of ethylene oxide with 1 mol of a primary alcohol having from 9 to 15 carbon atoms.

As builder substance C) there come into consideration, for example, alkali metal phosphates, especially tripolyphosphates, carbonates or hydrogen carbonates, especially their sodium salts, silicates, aluminosilicates, polycarboxylates, polycarboxylic acids, organic phosphonates, aminoalkylenepoly(alkylenephosphonates) or mixtures of those compounds.

Especially suitable silicates are sodium salts of crystalline layered silicates of the formula $NaHSi_tO_{2t+1} \cdot pH_2O$ or $Na_2Si_tO_{2t+1} \cdot pH_2O$ wherein t is a number from 1.9 to 4 and p is a number from 0 to 20.

Among the aluminosilicates, preference is given to those commercially available under the names zeolithe A, B, X and HS, and also to mixtures comprising two or more of those components. Zeolithe A is preferred.

Among the polycarboxylates, preference is given to polyhydroxycarboxylates, especially citrates, and acrylates and also copolymers thereof with maleic anhydride. Preferred poly-carboxylic acids are nitrilotriacetic acid, ethylenediaminetetraacetic acid and ethylene-diamine disuccinate either in racemic form or in the enantiomerically pure (S,S) form.

As component D) especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid, amino-trimethylene-phosphonic acid, as well as mixtures thereof and the salts therefrom.

As the peroxide component E) there come into consideration, for example, the organic and inorganic peroxides known in the literature and available commercially that bleach textile materials at conventional washing temperatures, for example at from 10 to 95° C.

In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperacetates, diperoxypersebacates, diperoxyphthalates and/or diperoxydodecanedioates, especially their corresponding free acids, are of interest. It is also possible to use peroxy acid precursors in combination with $H_2O_2$. Especially preferred are mono- or polyperoxide, especially organic peracids or their salts such as phthalimidoperoxycapronic acid, peroxybenzic acid, peracetic acid, diperoxydodecandiacid, diperoxynonandiacid, diperoxydecandiacid, diperoxyphthalic acid or their salts.

The amount of peroxide in the washing, cleaning, disinfecting or bleaching agent is preferably 0.5–30 wt-%, preferably 1–20 wt-% and more preferably 1–15 wt-%. In case a peroxide is used, the lower limit is preferably 2 wt-%, especially 5 wt-%.

Preferably, however, inorganic peroxides are used, for example persulfates, perborates, percarbonates and/or persilicates. It will be understood that mixtures of inorganic and/or organic peroxides can also be used. The peroxides may be in a variety of crystalline forms and have different water contents, and they may also be used together with other inorganic or organic compounds in order to improve their storage stability.

The peroxides are added to the washing, cleaning, disinfecting or bleaching agents preferably by mixing the components, for example using a screw metering system and/or a fluidised bed mixer.

The washing or cleaning agents may comprise, in addition to the combination according to the invention, one or more optical brighteners, for example from the class bis-triazinylamino-stilbenedisulfonic acid, bis-triazolyl-stilbenedisulfonic acid, bis-styryl-biphenyl or bis-benzofuranylbiphenyl, a bis-benzoxalyl derivative, bis-benzimidazolyl derivative or coumarin derivative or a pyrazoline derivative.

The washing or cleaning agents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; photobleaching agents; pigments; and/or shading agents. These constituents should, of course, be stable to any bleaching system employed. Such auxiliaries can be present in an amount of, for example, 0.1 to 20 wt-%, preferably 0.5 to 10 wt-%, especially 0.5 to 5 wt-%, based on the total weight of the washing or cleaning agent.

Furthermore, the washing, cleaning, disinfecting or bleaching agent can optionally contain enzymes. Enzymes can be added to washing, cleaning disinfecting or bleaching agent for stain removal. The enzymes usually improve the performance on stains that are either protein- or starch-based, such as those caused by blood, milk, grass or fruit juices. Preferred enzymes are cellulases, proteases, amylases and lipases. Preferred enzymes are cellulases and proteases, especially proteases. Cellulases are enzymes which act on cellulose and its derivatives and hydrolyze them into glucose, cellobiose, cellooligosaccharide. Cellulases remove dirt and have the effect of mitigating the roughness to the touch. Examples of enzymes to be used include, but are by no means limited to, the following:

proteases as given in U.S. Pat. No. 6,242,405, column 14, lines 21 to 32;

lipases as given in U.S. Pat. No. 6,242,405, column 14, lines 33 to 46;

amylases as given in U.S. Pat. No. 6,242,405, column 14, lines 47 to 56; and cellulases as given in U.S. Pat. No. 6,242,405, column 14, lines 57 to 64.

The enzymes can optionally be present in the washing, cleaning, disinfecting or bleaching agents. When used, the enzymes are usually present in an amount of 0.01–5 wt-%, preferably 0.05–5 wt-% and more preferably 0.1–4 wt-%, based on the total weight of the washing, cleaning disinfecting or bleaching agent.

In addition to the new crystal modification of Mn(III) saltren (compound (2)) it is also possible to use further transition metal salts or complexes known as bleach-activating active ingredients and/or conventional bleach activators, that is to say compounds that, under perhydrolysis conditions, yield unsubstituted or substituted perbenzo- and/or peroxo-carboxylic acids having from 1 to 10 carbon atoms, especially from 2 to 4 carbon atoms. Suitable bleach activators include the customary bleach activators, mentioned at the beginning, that carry O— and/or N-acyl groups having the indicated number of carbon atoms and/or unsubstituted or substituted benzoyl groups. Preference is given to polyacylated alkylenediamines, especially tetraacetylethylenediamine (TAED), acylated glycolurils, especially tetraacetylglycoluril (TAGU), N,N-diacetyl-N,N-dimethylurea (DDU), acylated triazine derivatives, especially 1,5-diacetyl-2,4-dioxohexahydro-1,3,5-triazine (DADHT), compounds of formula (3):

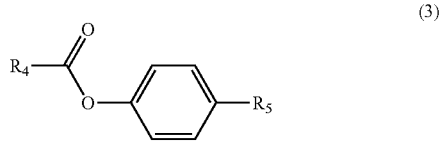

(3)

wherein $R_4$ is a sulfonate group, a carboxylic acid group or a carboxylate group, and wherein $R_5$ is linear or branched $(C_7–C_{15})$alkyl, especially activators known under the names SNOBS, SLOBS and DOBA, acylated polyhydric alcohols, especially triacetin, ethylene glycol diacetate and 2,5-diacetoxy-2,5-dihydrofuran, and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-4443177. Nitrile compounds that form perimine acids with peroxides also come into consideration as bleach activators.

Further preferred additives to the washing or cleaning agents according to the invention are dye fixing agents and/or polymers which, during the washing of textiles, prevent staining caused by dyes in the washing liquor that have been released from the textiles under the washing conditions. Such polymers are preferably polyvinylpyrrolidones, polyvinylimidazole, polyvinylpyridine-N-oxides or polybetaines which may have been modified by the incorporation of anionic or cationic substituents, especially those having a molecular weight in the range of from 5000 to 60000, more especially from 10000 to 50000. Such polymers are usually used in an amount of from 0.01 to 5 wt-%, preferably 0.05 to 5 wt-%, especially 0.1 to 2 wt-%, based on the total weight of the washing or cleaning agent t agent. Preferred polymers are those given in WO-A-02/02865 (see especially page 1, last paragraph and page 2, first paragraph).

The above mentioned washing or cleaning agents can take a variety of physical forms including powder, granular, tablet and liquid forms. Examples thereof are conventional powder heavy-duty detergents, compact and supercompact heavy-duty detergents and tablets, like heavy-duty detergent tablets. One important physical form is the so-called concentrated granular form adapted to be added to a washing machine.

Of importance are also the so-called compact (or supercompact) detergents. In the field of detergent manufacture, a trend has developed recently towards the production of compact detergents, which contain increased amounts of active substance. In order to minimize energy expenditure during the washing process, the compact detergents are required to operate efficiently at temperatures as low as 40° C., or even at room temperatures, e.g. at 25° C. Such detergents usually contain only low amounts of fillers or processing aids, like sodium sulfate or sodium chloride. The amount of such fillers is usually 0–10 wt-%, preferably 0–5 wt-%, especially 0–1 wt-%, based on the total weight of the detergent agent. Such detergents usually have a bulk density of 650–1000 g/l, preferably 700–1000 g/l and especially 750–1000 g/l.

The washing or cleaning agents can also be present in the form of tablets. Relevant characteristics of tablets are ease of dispensing and convenience in handling. Tablets are the most compact delivery of solid detergents and have a bulk density of, for example, 0.9 to 1.3 kg/liter. To enable fast disintegration laundry detergent tablets generally contain special disintegrants:

Effervescents such as carbonate/hydrogencarbonate/citric acid;

swelling agents like cellulose, carboxymethyl cellulose, cross-linked poly(N-vinylpyrrollidone);

quickly dissolving materials such as Na (K) acetate, or Na (K) citrate;

rapidly dissolving water-soluble rigid coating such as dicarboxy acids.

The tablets can also contain combinations of any of the above disintegrants.

The washing or cleaning agents may also be formulated as an aqueous liquid comprising 5–50 wt-%, preferably 10–35 wt-% water or as a non-aqueous liquid detergent, containing not more than 5 wt-%, preferably 0–1 wt-% of water, based on the total weight of the washing or cleaning agent. Non-aqueous liquid detergent compositions can contain other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5 to 90 wt-%, typically 10 to 50 wt-% of such carriers, based on the total weight of the detergent agent. The detergents can also be present as the so-called "unit liquid dose" form.

The washing or cleaning agents are usually formulated that the washing liquor has pH value of about 6.5–11, preferably 7.5–11 during the whole washing procedure. The liquor ration in the washing process is usually 1:4 to 1:40, preferably 1:4 to 1:15, more preferably 1:4 to 1:10, especially preferably 1:5 to 1:9.

The washing procedure is usually done in washing machine.

There are various types of washing machines, for example:
- top-loader-washing machines with a verticle rotating axis; these machines, which have usually a capacity of about 45 to 83 liters, are used for washing processes at temperatures of 10–50° C. and washing cycles of about 10–60 minutes. Such types of washing machines are often used in the USA;
- front-loader-washing machines with a horizontal rotating axis; these machines, which have usually a capacity of about 8 to 15 liters, are used for washing processes at temperatures of 30–95° C. and washing cycles of about 10–60 minutes. Such types of washing machines are often used in Europe;
- top-loader-washing machines with a verticle rotating axis; these machines, which have usually a capacity of about 26 to 52 liters, are used for washing processes at temperatures of 5–25° C. and washing cycles of about 8–15 minutes. Such types of washing machines are often used in Japan.

The washing, cleaning, disinfecting or bleaching agent according to the invention can also be used in a soaking process, where the stained textiles are left for 0.5–24 hours in a solution or suspension of the detergent and/or bleaching laundry additive without agitation. Soaking can take place for example in a bucket or in a washing machine. Usually the textiles are washed and/or rinsed after the soaking process.

It is also possible that the new crystal modification of the 1:1 manganese (III) complex of N,N',N"-tris[salicylideneaminoethyl]amine (compound (2)) is incorporated into a granule, which comprise suitable granulation auxiliaries. Such granules are suitable for incorporation into a powder- or granule-form washing, cleaning, disinfecting or bleaching agent.

Surprisingly, the new crystal modification of Mn(III) saltren (compound (2)) also exhibits a markedly improved bleach-catalysing action on coloured stains which occur on wall or floor tiles, even at low temperature.

The use of the new crystal modification of Mn(III)saltren (compound (2)) as catalysts for reactions with peroxy compounds in cleaning solutions for hard surfaces, especially for wall or floor tiles, is therefore of special interest.

The new crystal modification of Mn(III)saltren (compound (2)) also has, together with peroxy compounds, excellent antibacterial action. The use of the new crystal modification of Mn(III)saltren (compound (2)) for killing bacteria or for protecting against bacterial attack is therefore likewise of interest.

The new crystal modification of Mn(III)saltren (compound (2)) are also outstandingly suitable for selective oxidation in the context of organic synthesis, especially the oxidation of organic molecules, e.g. of olefins to form epoxides. Such selective transformation reactions are required especially in process chemistry. The invention accordingly relates also to the use of the metal complex compounds of formula (1) in selective oxidation reactions in the context of organic synthesis.

The new crystal modification of the 1:1 manganese (III) complex of N,N',N"-tris[salicylideneaminoethyl]amine (compound (2)) is obtainable by α) adding a solution comprising 3 parts of salicylaldehyd and 1 part of tris-(2-aminoethyl) amine to a Mn(III) solution, which can optionally comprise some amount of a base, such as NaOH, KOH, etc. . . and β) isolation and purification of the 1:1 manganese (III) complex of N,N',N"-tris[salicylideneaminoethyl]amine (compound (2)).

Suitable organic solvents for step α) are DMF, N-methylpyrrolidone, Dimethylsufoxide or alcohols such as methanol, ethanol, butanol etc. . . .

The reaction temperature for step α) are preferably between 15–50° C., more preferably between 20–40° C., most preferably room temperature (25° C.).

The isolation and purification (step β) is done by conventional means. Preferably, the compound is filtrated, washed with some amount of the solvent and dried in vacuum.

The present invention is illustrated but in no way limited by the following examples.

EXAMPLE 1

To an ethanolic solution comprising 3 parts of salicylic aldehyde, 1 part of tris-(2-aminoethyl)-amine and 2 equivalents of a NaOH-solution (50%), which has been stirred at 25° C., a stoichiometric amount of an ethanolic Mn(III)salt solution is added. The Mn(III)saltren with new crystal form is obtained after a few minutes. The precipitated compound is filtered off, washed and dried in vacuum.

EXAMPLE 2

3 parts of salicylic aldehyde and 1 part of tris-(2-aminoethyl)amine are solved in DMF. This solution is stirred for 20 h at a temperature of 25° C. Afterwards, the Mn(III)salt solved in DMF is added. Simultaneously, 1 wt-% of a Mn(III)saltren seed crystal, obtainable according to Example 1 is also added to the solution. The Mn(III)saltren with new crystal form is obtained after a few minutes. The precipitated compound is filtered off, washed and dried in vacuum.

EXAMPLES 3–26

In Table 3a, 3b and 3c we show examples for compositions of detergents and laundry bleaching additives, containing the Mn(III)saltren with new crystal form (Examples 3–26)

TABLE 3a

Ingredients of detergent powders and laundry bleaching additives

| Ingredients | A | B | C | D |
|---|---|---|---|---|
| Sodium laurylbenzene-sulfonate (LAS) | 8% | 8% | 8% | 10% |
| Sodium lauryl ether sulfate (AES) | 3% | 3% | 3% | 3% |
| Dobanol 23–6.5 (non-ionic alcoholethoxylate) | 5% | 5% | 5% | 4% |
| Zeolite A | 22% | 22% | 20% | — |
| Polycarboxylate (co-builder) | 5% | 5% | 5% | — |
| Sodium tripolyphosphate | — | — | — | 30% |
| Soda ash | 21% | 21% | 21% | 17% |
| Sodium silicate | 4% | 4% | 4% | 5% |
| Sodium sulfate | 5% | 5% | 5% | 14% |
| Hydroxyethanediphosphonic acid (complexing agent) | 0.5% | 0.5% | 0.5% | — |
| Cellulase | 1.5% | — | — | — |
| Protease | — | 1.5% | 1.5% | — |
| Carboxymethylcellulose | 1% | 1% | 1% | 2% |
| Sodium percarbonate | 15% | 15% | 15% | 10% |
| TAED | — | — | 2.5% | — |
| polyvinylpyrrolidone | — | — | — | — |
| Soap | 2% | 2% | 2% | — |
| Fluorescent whitening agent | 0.1% | 0.1% | 0.1% | 0.2% |
| Perfume | 0.1% | 0.1% | 0.1% | 0.1% |
| Granule: | | | | |
| The Mn(III)saltren with new crystal modification | X% | X% | X% | X% |
| PEG 8000 | 1.5 * X% | 1.5 * X% | 1.5 * X% | 1.5 * X% |
| $TiO_2$ | 1.5 * X% | 1.5 * X% | 1.5 * X% | 1.5 * X% |
| $CaSO_4$ | 3 * X% | 3 * X% | 3 * X% | 3 * X% |
| Maize starch | 3 * X% | 3 * X% | 3 * X% | 3 * X% |

In each of the above detergents a sufficient amount of water is used to give 100%.

TABLE 3b

Ingredients of detergent powders and laundry bleaching additives

| Ingredients | E | F | G | H |
|---|---|---|---|---|
| Sodium laurylbenzene-sulfonate (LAS) | 8% | — | 5% | — |
| Sodium lauryl ether sulfate (AES) | 3% | — | 1% | — |
| Dobanol 23–6.5 (non-ionic alcoholethoxylate) | 5% | — | 2% | — |
| Zeolite A | 22% | — | 12% | — |
| Polycarboxylate (co-builder) | 5% | — | 2% | — |
| Sodium tripolyphosphate | — | — | — | — |
| Soda ash | 21% | 45% | 11% | — |
| Sodium silicate | 4% | — | — | — |
| Sodium sulfate | 5% | — | 2% | — |
| Hydroxyethanediphosphonic acid (complexing agent) | 0.5% | — | — | — |
| Cellulase | — | — | — | — |
| Protease | 1.5% | — | 1% | — |
| Carboxymethylcellulose | 2% | — | 0.4% | — |
| Sodium percarbonate | 15% | 50% | 60% | 95% |
| TAED | — | — | — | — |
| polyvinylpyrrolidone | 1% | — | — | — |
| Soap | 2% | — | — | — |
| Fluorescent whitening agent | 0.1% | — | 0.1% | 0.1% |
| Perfume | 0.1% | 0.1% | 0.1% | 0.1% |
| Granule: | | | | |
| The Mn(III)saltren with new crystal modification | X% | X% | X% | X% |
| PEG 8000 | 1.5 * X% | 1.5 * X% | 1.5 * X% | 1.5 * X% |
| $TiO_2$ | 1.5 * X% | 1.5 * X% | 1.5 * X% | 1.5 * X% |
| $CaSO_4$ | 3 * X% | 3 * X% | 3 * X% | 3 * X% |
| Maize starch | 3 * X% | 3 * X% | 3 * X% | 3 * X% |

In each of the above detergents a sufficient amount of water is used to give 100%.

In Tables 3a and 3b, the Mn(III)saltren with the new crystal modification forms a granule together with PEG 8000, TiO$_2$, CaSO$_4$ and maize starch.

TABLE 3c (Laundry product compositions)

| Examples | Amount X of the Mn(III)saltren with new crystal form used (see Table 1a) | Laundry product from table 1a |
|---|---|---|
| 3 | 0.05% | A |
| 4 | 0.1% | A |
| 5 | 0.3% | A |
| 6 | 0.05% | B |
| 7 | 0.1% | B |
| 8 | 0.3% | B |
| 9 | 0.05% | C |
| 10 | 0.1% | C |
| 11 | 0.3% | C |
| 12 | 0.05% | D |
| 13 | 0.1% | D |
| 14 | 0.3% | D |
| 15 | 0.05% | E |
| 16 | 0.1% | E |
| 17 | 0.3% | E |
| 18 | 0.05% | F |
| 19 | 0.1% | F |
| 20 | 0.3% | F |
| 21 | 0.05% | G |
| 22 | 0.1% | G |
| 23 | 0.3% | G |
| 24 | 0.05% | H |
| 25 | 0.1% | H |
| 26 | 0.3% | H |

EXAMPLE 27

Use of The Mn(III)saltren with new crystal form as a bleaching catalyst in a laundry bleaching process.

A cloth of 3 g of tea-stained cotton (BC-1, CFT, Holland) is washed in 300 ml of bleach liquor. The bleach liquor contains 0.71 g of sodium carbonate and 0.75 g of sodium percarbonate. The water hardness corresponds to 50 ppm of CaCO$_3$. The liquor contains optionally 0.004 g of the Mn(III)saltren with new crystal form as a bleaching catalyst. The Mn(III)saltren with new crystal form is added in the form of a granule, containing 10% of the Mn(III)saltren with new crystal form and 90% formulation auxiliaries.

The bleaching is conducted in beakers in a LINITEST apparatus at 25° C. over 30 minutes. After bleaching the cloth is rinsed and ironed and the reflection spectrum measured with a SPECTRAFLASH 2000 instrument and are transformed into brightness Y values according to the CIE standard procedure. The bleaching effect is given as DY=Y (after washing)−Y(before washing).

The results obtained are set out in the following Table 4. The results demonstrate the bleching effect of the Mn(III) saltren complex with new crystal structure.

TABLE 4

| Composition of bleaching liquor | DY |
|---|---|
| no Mn(III)saltren complex | 8.8 |
| 0.004 g of Mn(III)saltren complex with new crystal form | 13.5 |

BRIEF DESCRIPTION OF THE DRAWINGS

FIG. 1: shows the powder X-ray diffraction pattern of Mn(III)saltren (compound (2)), obtained from Example 1. The powder sample of the new crystal modification of Mn(III)saltren (compound (2)) has been analysed by a STOE-powder-diffractometer at room temperature (25° C.) under Cu X-ray [λ(CuKα)=1.540598 Å].

FIG. 2. shows the powder X-ray diffraction pattern of Mn(III)saltren (compound (2)), obtained from Example 2. The powder sample of the new crystal modification of Mn(III)saltren (compound (2)) has been analysed by a STOE-powder-diffractometer at room temperature (25° C.) under Cu X-ray [λ(CuKα)=1.540598 Å].

The invention claimed is:

1. A crystal modification of the 1:1 manganese (III) complex of N,N',N"-tris[salicylideneaminoethyl]amine

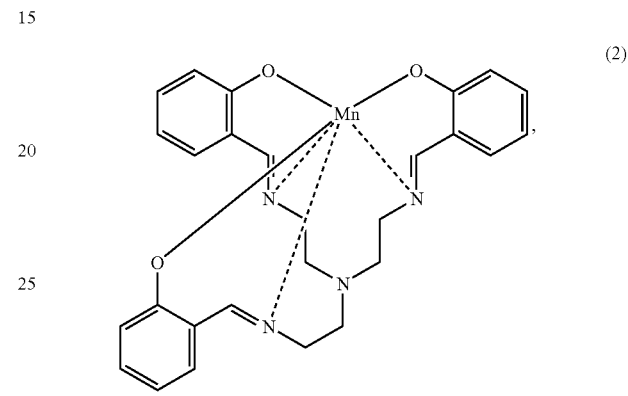

(2)

characterized by a peak at a d-spacing of about 6.87 Å in its powder X-ray diffraction pattern.

2. A crystal modification of 1:1 manganese (III) complex of N,N',N"-tris[salicylideneaminoethyl]amine (compound (2)) according to claim 1, characterized by a peak at d-spacing of about 6.87 Å and further characterized by d spacing at about 12.69 Å in its powder X-ray diffraction pattern.

3. A crystal modification of 1:1 manganese (III) complex of N,N',N"-tris[salicylideneaminoethyl]amine (compound (2)) according to claim 2, characterized by peaks at d-spacings of about 6.87 and 12.89 Å and further characterized by peaks of about 3.51, 3.65, 4.20, 4.63, 4.95, 5.30, 6.38, 7.50, and 10.57 Å in its powder X-ray diffraction pattern.

4. A crystal modification of the 1:1 manganese (III) complex of N,N',N"-tris[salicylideneaminoethyl]amine (compound (2)) according to claim 3, characterized by peaks at d-spacings of about 3.51, 3.65, 4.20, 4.63, 4.95, 5.30, 6.38, 6.87, 7.50, 10.57 and 12.69 Å and further characterized by peaks of about 2.22, 2.48, 2.94, 3.14, 3.76, 3.94, 5.82, 6.19, and 8.59 Å in its powder X-ray diffraction pattern.

5. A crystal modification of 1:1 manganese (III) complex of N,N',N"-tris[salicylideneaminoethyl]amine (compound (2)) according to claim 4, which has a characteristic X-ray powder pattern obtained by X-ray diffraction on a powder sample of the crystal modification in a STOE-powder-diffractometer at room temperature (25° C.) under Cu X-ray [λ(CuKα)=1.540598 Å] represented by the following spacings between lattice planes:

| d(Å) | Intensity |
|---|---|
| 12.69 | strong |
| 10.57 | medium |
| 8.59 | weak |
| 7.50 | medium |

-continued

| d(Å) | Intensity |
|---|---|
| 6.87 | strong |
| 6.38 | medium |
| 6.19 | weak |
| 5.82 | weak |
| 5.30 | medium |
| 4.95 | medium |
| 4.63 | medium |
| 4.20 | medium |
| 3.94 | weak |
| 3.76 | weak |
| 3.65 | medium |
| 3.51 | medium |
| 3.14 | weak |
| 2.94 | weak |
| 2.48 | weak |
| 2.22 | weak. |

6. A crystal modification of 1:1 manganese (III) complex of N,N',N''-tris[salicylideneaminoethyl]amine (compound (2)) according to claim 1, characterized in accordance with X-ray diffraction on its sample single crystal that it is represented by the following basic crystallographic data:

| | |
|---|---|
| Crystal system | monoclinic |
| Space group | P 2$_1$/n |
| a[Å] | 7.906 |
| b[Å] | 25.609 |
| c[Å] | 11.736 |
| α[°] | 90 |
| β[°] | 96.55 |
| γ[°] | 90 |
| V[Å$^3$] | 2360.6 |
| Structure unit per cell (Z) | 4 |
| Absorption coefficient μ [mm$^{-1}$] | 0.597 |
| Crystal system | monoclinic |
| F(000) | 1064. |

7. A method of catalyzing oxidation reactions comprising incorporating into a reaction mixture a catalytically effective amount of the crystal modification of the 1:1 manganese (III) complex of N,N',N''-tris[salicylideneaminoethyl]amine (compound (2)) according to claim 1.

8. A method according to claim 7, wherein the crystal modification of the 1:1 manganese (III) complex of N,N',N''-tris[salicylideneaminoethyl]amine is used in a washing, cleaning, disinfecting or bleaching agent.

9. A method according to claim 8, wherein the crystal modification of the 1:1 manganese (III) complex of N,N',N''-tris[salicylideneaminoethyl]amine is used in combination with a peroxy compound for the bleaching of spots or stains on textile material or for the prevention of the redeposition of migrating dyes in the context of a washing process of textile materials.

10. A method according to claim 8, wherein the crystal modification of the 1:1 manganese (III) complex of N,N',N''-tris[salicylideneaminoethyl]amine is used as a catalyst for reactions with a peroxy compound for bleaching in the context of paper-making.

11. A washing, cleaning, disinfecting or bleaching agent, containing

I) 0–50% by weight, A) of at least one anionic surfactant and/or B) of at least non-ionic surfactant, II) 0–70% by weight, C) of at least one builder substance, III) 0–10% by weight, D) of at least one (poly)phosponate and/or aminoalkylene-poly(alkylenephosphonate), IV) 1–99% by weight, E) of at least one peroxide and/or of at least one peroxide-forming substance, and V) F) the crystal modification of the 1:1 manganese (III) complex of N,N',N''-tris[salicylideneaminoethyl]amine (compound (2)) according to claim 1 whereby when 0.2 to 20 g/liter of the washing, cleaning, disinfecting and bleaching agent are added to a liquor, a concentration of 0.2–50 mg/liter of compound (2) in the liquor is provided.

12. A process for the preparation of the modification of the 1:1 manganese (III) complex of N,N',N''-tris[salicylideneaminoethyl]amine (compound (2)) according to claim 1 by a) adding a solution comprising 3 parts of salicylic aldehyde and 1 part of tris-(2-aminoethyl)amine to a Mn(III) solution, which can optionally comprise some amount of a base, and b) isolation and purification of the 1:1 manganese (III) complex of N,N',N''-tris[salicylideneaminoethyl]amine (compound (2)).

13. A washing, cleaning, disinfecting or bleaching agent according to claim 11, containing I) 0–30% by weight, A) of at least one anionic surfactant and/or B) of at least non-ionic surfactant, II) 0–50% by weight, C) of at least one builder substance, III) 0–5% by weight, D) of at least one (poly)phosponate and/or aminoalkylene-poly(alkylenephosphonate), IV) 1–70% by weight, E) of at least one peroxide and/or of at least one peroxide-forming substance, and V) F) the crystal modification of the 1:1 manganese (III) complex of N,N',N''-tris[salicylideneaminoethyl]amine (compound (2)), whereby when 0.2 to 20 g/liter of the washing, cleaning, disinfecting and bleaching agent are added to a liquor, a concentration of 0.2–30 mg/liter of compound (2) in the liquor is provided.

14. A method according to claim 8, wherein the crystal modification of the 1:1 manganese (III) complex of N,N',N''-tris[salicylideneaminoethyl]amine (compound (2)) is used in combination with a peroxy compound for the cleaning of hard surfaces.

* * * * *